United States Patent
Natori et al.

(10) Patent No.: US 11,408,027 B2
(45) Date of Patent: Aug. 9, 2022

(54) METHOD OF EVALUATING QUALITY OF MIRNA DERIVED FROM BODY FLUID

(71) Applicant: Toray Industries, Inc., Tokyo (JP)

(72) Inventors: Kazue Natori, Kamakura (JP); Satoko Kozono, Kamakura (JP); Satoshi Kondou, Kamakura (JP)

(73) Assignee: Toray Industries, Inc., Tokyo (JP)

(*) Notice: Subject to any disclaimer, the term of this patent is extended or adjusted under 35 U.S.C. 154(b) by 152 days.

(21) Appl. No.: 16/078,693

(22) PCT Filed: Feb. 21, 2017

(86) PCT No.: PCT/JP2017/006324
§ 371 (c)(1),
(2) Date: Aug. 22, 2018

(87) PCT Pub. No.: WO2017/146033
PCT Pub. Date: Aug. 31, 2017

(65) Prior Publication Data
US 2019/0048408 A1 Feb. 14, 2019

(30) Foreign Application Priority Data
Feb. 22, 2016 (JP) .............................. JP2016-030904

(51) Int. Cl.
| | |
|---|---|
| *C12Q 1/6837* | (2018.01) |
| *G16B 25/00* | (2019.01) |
| *G01N 33/53* | (2006.01) |
| *C12N 15/113* | (2010.01) |
| *C12N 15/09* | (2006.01) |
| *C12Q 1/6876* | (2018.01) |
| *G01N 33/50* | (2006.01) |
| *G01N 37/00* | (2006.01) |
| *C12M 1/00* | (2006.01) |
| *C12Q 1/68* | (2018.01) |
| *C12Q 1/6883* | (2018.01) |
| *G16B 25/10* | (2019.01) |

(52) U.S. Cl.
CPC ............ *C12Q 1/6837* (2013.01); *C12M 1/00* (2013.01); *C12N 15/09* (2013.01); *C12N 15/113* (2013.01); *C12Q 1/68* (2013.01); *C12Q 1/6876* (2013.01); *C12Q 1/6883* (2013.01); *G01N 33/50* (2013.01); *G01N 33/53* (2013.01); *G01N 37/00* (2013.01); *G16B 25/00* (2019.02); *G16B 25/10* (2019.02)

(58) Field of Classification Search
CPC ........ C12M 1/00; C12N 15/09; C12N 15/113; C12N 1/00; C12Q 1/68; C12Q 2600/178; G01N 33/53
See application file for complete search history.

(56) References Cited

U.S. PATENT DOCUMENTS

| | | |
|---|---|---|
| 2009/0075258 A1 | 3/2009 | Latham et al. |
| 2012/0253687 A1 | 10/2012 | Kuroda et al. |
| 2013/0309680 A1 | 11/2013 | Morley et al. |
| 2014/0272993 A1 | 9/2014 | Van Keuren-Jensen et al. |

FOREIGN PATENT DOCUMENTS

| | | |
|---|---|---|
| EP | 2 942 399 A1 | 11/2015 |
| JP | 2008-35779 A | 2/2008 |
| JP | 2011-200220 A | 10/2011 |
| JP | 2015-519045 A | 7/2015 |
| WO | 2012/068288 A2 | 5/2012 |
| WO | 2012/068288 A3 | 5/2012 |

OTHER PUBLICATIONS

Cerdá-Olmedo et al. (PLoS ONE 10(3): e0121903, 2015, pp. 1-14).*
Exiqon custom *Homo sapiens* miRNA array, Comment[ArrayExpressReleaseDate] Nov. 2, 2011, pp. 1-14.*
Carlsen et al. (Arthritis Rheum. May 2013; 65(5): 1324-1334).*
Cerdá-Olmedo et al. (PLoS ONE 10(3): e0121903, 2015, pp. 1-14). Only Supplementary Data attached.*
Carlsen et al. (Arthritis Rheum. May 2013; 65(5): 1324-1334). Only Supplementary Data attached.*
Arraztio, A., "Identification of a MicroRNA signature for Fibromyalgia diagnosis," *Being bio-reactive*, 2015 https://being-bioreactive.com/2015/06/09/identification-of-a-microrna-signature-for-fibromyalgia-diagnosis/.
The Extended European Search dated Sep. 30, 2019, of counterpart European Application No. 17756471.3.
Zhao Q, Chen et al., "Self-assembled virus-like particles from rotavirus structural protein VP6 for targeted drug delivery", *Bioconjug Chem*. Mar. 16, 2011, 22(3):346-52.

* cited by examiner

*Primary Examiner* — Terra C Gibbs
(74) *Attorney, Agent, or Firm* — DLA Piper LLP (US)

(57) ABSTRACT

A method of evaluating quality of miRNA derived from a body fluid sample includes a measuring step; comparing a measured value(s) of the abundance(s) of the one or more reference miRNAs in a body fluid sample or a representative value thereof to a measured value(s) of the abundance(s) of the one or more reference miRNAs in a standard body fluid sample or a representative value thereof, to obtain a difference(s) or a ratio(s) of the measured value(s) of the abundance(s) of the one or more reference miRNAs or the representative value thereof between the body fluid sample and the standard body fluid sample; and judging the quality of the miRNA derived from the body fluid sample based on the difference(s) or the ratio(s) of the measured value(s) of the abundance(s) of the one or more reference miRNAs or the representative value thereof obtained in the comparing step.

7 Claims, No Drawings
Specification includes a Sequence Listing.

METHOD OF EVALUATING QUALITY OF MIRNA DERIVED FROM BODY FLUID

TECHNICAL FIELD

This disclosure relates to a method of evaluating the quality of miRNA derived from a body fluid sample.

BACKGROUND

A miRNA (microRNA) is transcribed as an RNA (precursor) having a hairpin-like structure from genomic DNA. The precursor is cleaved by a particular enzyme, dsRNA cleavage enzyme (Drosha, Dicer) having RNase III cleavage activity, and converted into a double-stranded form and then into single strands. It is thought that the antisense strand, which is one of the double-strands, is incorporated into a protein complex called RISC, and that the RISC is involved in suppression of translation of mRNA. Thus, miRNA takes various forms in the various stages after its transcription. Therefore, when a miRNA is to be detected, various forms including the hairpin structure, double-stranded structure, and single-stranded structure need to be taken into account. A miRNA is an RNA of 15 to 25 bases, and the presence of miRNAs has been confirmed in various organisms.

In recent years, it has been suggested that a large amount of miRNAs are present in not only cells, but also body fluids such as serum, plasma, urine, and spinal fluid, which are samples containing no cells, and that the expression levels of those miRNAs should become biomarkers for various diseases including cancers. As of February 2016, there are not less than 2500 kinds of miRNAs in humans and, when a gene expression assay system such as a highly sensitive DNA microarray is used, expression of more than 1000 kinds of miRNAs among them can be detected simultaneously in serum or plasma. Thus, many studies are being carried out to find biomarkers by DNA microarray in body fluids such as serum/plasma, urine, and spinal fluid, and development of biomarker tests that enable early detection of diseases is expected.

On the other hand, RNA is a substance whose degradation easily occurs by various physical and chemical factors such as heat, degradative enzymes, and freeze-thawing, and it is known that degradation of RNA affects measurement of the expression level when carrying out gene expression analysis using a DNA microarray. In a test in which the expression level of miRNA contained in a body fluid is measured as a disease biomarker, if the test and diagnosis are carried out based on an inaccurate measured value of the expression level, the patient may miss the chance of an appropriate treatment, or may be forced to bear unnecessary economical and physical burdens due to application of incorrect medical care. Thus, for accurate measurement of the expression level, it is very important to use a sample in which the target miRNA to be tested is not degraded.

Conventionally, as a method of measuring the degree of RNA degradation, electrophoresis has been commonly used. For example, the measurement can be carried out based on the band intensity ratio (28S/18S) between a band derived from 28S ribosomal RNA and a band derived from 18S ribosomal RNA. As another method, JP 2015-519045 A proposes a method in which the degree of RNA degradation is quantified and evaluated based on the lengths of RNA segments, which method utilizes the characteristics of long-chain RNA that degradation of nucleotides leads to shortening of the segment lengths.

However, in many cases RNA in a short-chain fraction is used when the expression level of miRNA is measured and, in such cases, long-chain RNA is not contained therein. Therefore, conventional methods such as those described above cannot be effective methods of measuring the degree of RNA degradation. The degree of degradation of RNA used can also be measured based on correlation coefficients among the total genes obtained from the result of gene expression analysis. However, since that method requires data on the total genes, it takes a lot of time and labor. In view of this, a method focusing on degraded fragments derived from long-chain RNA, wherein the degree of degradation of miRNA in a short-chain fraction is evaluated using as an index the degraded fragments contained in the short-chain fraction has been developed (JP 2008-35779 A).

As described above, for accurate measurement of the expression level of target RNA, it is important to evaluate the quality by measuring the degree of degradation of RNA in the sample. However, the conventional methods described above are based on utilization of ribosomal RNA and long-chain RNA. Ribosomal RNA and long-chain RNA are RNAs present in nuclei and cytoplasm, and they are hardly present in body fluid samples such as serum, plasma, urine, and spinal fluid. Thus, those conventional methods are not capable of accurate measurement of the degree of degradation of miRNA contained in a body fluid sample and are, therefore, not capable of evaluation of the quality of miRNA.

It could therefore be helpful to provide a method of evaluating the quality of miRNA contained in a body fluid sample, which is not adapted for conventional evaluation methods, by measuring the degree of degradation of miRNA in the body fluid sample.

SUMMARY

We discovered that the quality of target miRNA can be evaluated by measuring the abundance of miRNA (hereinafter referred to as "reference miRNA") whose abundance changes depending on degradation of a nucleic acid sample contained in a body fluid sample. Our method evaluates the quality of miRNA by using at least any one of the miRNAs of SEQ ID NOs:1 to 12 as a reference miRNA(s), and compares the abundance(s) of the reference miRNA(s) in a body fluid sample with the abundance(s) of the miRNA(s) in a standard body fluid sample that is in a state where degradation of the nucleic acid sample has not proceeded.

We thus provide:

(1) A method of evaluating the quality of miRNA derived from a body fluid sample, the method comprising:

a measuring step of using miRNA-containing RNA samples prepared from a body fluid sample and a standard body fluid sample to measure the abundance(s) of one or more reference miRNAs selected from miRNAs consisting of the base sequences of SEQ ID NOs:1 to 12 in each of the body fluid sample and the standard body fluid sample;

a comparing step of comparing a measured value(s) of the abundance(s) of the one or more reference miRNAs in the body fluid sample or a representative value thereof with a measured value(s) of the abundance(s) of the one or more reference miRNAs in the standard body fluid sample or a representative value thereof, to obtain a difference(s) or a ratio(s) of the measured value(s) of the abundance(s) of the one or more reference miRNAs or the representative value thereof between the body fluid sample and the standard body fluid sample; and a judging step of judging the quality of the miRNA derived from the body fluid sample based on the difference(s) or the ratio(s) of the measured value(s) of the abundance(s) of the one or more reference miRNAs or the representative value thereof obtained in the comparing step.

(2) The method according to (1), wherein the comparing step is a step of obtaining a difference or a ratio of the measured value of the abundance of one reference miRNA, differences or ratios of the measured values of the abundances of a plurality of reference miRNAs, respectively, or a difference or a ratio of the representative value of the measured values of the abundances of a plurality of reference miRNAs.

(3) The method according to (1) or (2), wherein the judging step comprises comparing the difference(s) or the ratio(s) of the measured value(s) of the abundance(s) of the one or more reference miRNAs with a threshold(s) predetermined as a criterion(criteria).

(4) The method according to any one of (1) to (3), wherein the comparing step comprises subtracting the measured value(s) of the abundance(s) in the standard body fluid sample or the representative value thereof from the measured value(s) of the abundance(s) in the body fluid sample or the representative value thereof to calculate the difference(s), or dividing the measured value(s) of the abundance(s) in the body fluid sample or the representative value thereof by the measured value(s) of the abundance(s) in the standard body fluid sample or the representative value thereof to calculate the ratio(s).

(5) The method according to (4), wherein the judging step comprises comparing the difference(s) or the ratio(s) of the measured value(s) of the abundance(s) of the one or more reference miRNAs or the representative value thereof with a threshold(s) predetermined as a reference(s), wherein when the difference(s) or the ratio(s) exceed(s) the threshold(s), the quality of the miRNA derived from the body fluid sample is judged to be good.

(6) The method according to any one of (1) to (5), wherein the representative value of the measured values of the abundances of the plurality of reference miRNAs in each of the body fluid sample and the standard body fluid sample is an average or a median of the measured values of the abundances of the plurality of reference miRNAs.

(7) The method according to any one of (1) to (6), wherein the measuring step comprises correcting the measured value(s) of the abundance(s) of the one or more reference miRNAs in each of the body fluid sample and the standard body fluid sample, and the subsequent steps are carried out using the measured value(s).

(8) The method according to any one of (1) to (7), wherein the measuring step comprises carrying out hybridization by bringing a probe(s) for capturing the one or more reference miRNAs, the probe(s) being immobilized on a support, into contact with each of nucleic acid samples which are extracted from the body fluid sample and the standard body fluid sample and labeled with a labeling substance, respectively, to measure the abundance(s) of the one or more reference miRNAs in each of the body fluid sample and the standard body fluid sample.

(9) The method according to any one of (1) to (8), wherein the measuring step comprises measuring the abundance(s) of a target miRNA(s) in the body fluid sample concurrently with the measurement of the abundance(s) of the one or more reference miRNA(s) in the body fluid sample.

(10) The method according to (9), wherein the measuring step comprises correcting the measured value(s) of the abundance(s) of the target miRNA(s) in the body fluid sample.

(11) The method according to (9) or (10), wherein the measuring step comprises carrying out hybridization by bringing a probe(s) for capturing the target miRNA(s) and a probe(s) for capturing the one or more reference miRNAs, the probes being immobilized on a support, into contact with a nucleic acid sample which is extracted from the body fluid sample and labeled with a labeling substance, to measure the abundance of each of the target miRNA(s) and the one or more reference miRNAs in the body fluid sample.

(12) The method according to any one of (1) to (11), wherein the body fluid sample is blood, serum, or plasma.

(13) A program(s) that evaluates the quality of miRNA derived from a body fluid sample, the program(s) causing one or more computers to execute:
a measured value-obtaining step of obtaining a measured value(s) of the abundance(s) of one or more reference miRNAs selected from miRNAs consisting of the base sequences of SEQ ID NOs:1 to 12 in each of a body fluid sample and a standard body fluid sample, the measured value(s) being measured by using miRNA-containing RNA samples prepared from the body fluid sample and the standard body fluid sample;
a comparing step of comparing a measured value(s) of the abundance(s) of the one or more reference miRNAs in the body fluid sample or a representative value thereof with a measured value(s) of the abundance(s) of the one or more reference miRNAs in the standard body fluid sample or a representative value thereof, to obtain a difference(s) or a ratio(s) of the measured value(s) of the abundance(s) of the one or more reference miRNAs or the representative value thereof between the body fluid sample and the standard body fluid sample; and
a judging step of judging the quality of the miRNA derived from the body fluid sample based on the difference(s) or the ratio(s) of the measured value(s) of the abundance(s) of the one or more reference miRNAs or the representative value thereof obtained in the comparing step.

(14) A computer-readable recording medium in which the program(s) according to (13) is/are recorded.

(15) A chip for miRNA quality evaluation, comprising a support on which a probe(s) that captures one or more reference miRNAs selected from miRNAs consisting of the base sequences of SEQ ID NOs:1 to 12 is/are immobilized.

(16) A chip for miRNA expression analysis, comprising a support on which a probe(s) that captures a target miRNA(s) and a probe(s) for capturing one or more reference miRNAs selected from miRNAs consisting of the base sequences of SEQ ID NOs:1 to 12 are immobilized.

We enable evaluation of the quality of miRNA contained in a body fluid sample, which has been difficult by conventional methods. Since we enable accurate and simple evaluation of, for example, whether a body fluid sample has a quality suitable for gene expression analysis using miRNA, a more accurate test for a disease becomes possible using as an index the expression level of a biomarker in a body fluid sample.

DETAILED DESCRIPTION

Our method evaluates the quality (degree of degradation) of miRNA derived from a body fluid sample, and the method comprises: a measuring step of measuring, using one or more miRNAs selected from miRNAs consisting of the base sequences of SEQ ID NOs:1 to 12 as a reference miRNA(s), the abundance(s) of the reference miRNA(s) in the body fluid sample and the abundance(s) of the reference miRNA(s) in a standard body fluid sample; a comparing step of obtaining the difference(s) or the ratio(s) between the measured value(s) of the reference miRNA(s) in the body fluid sample obtained in the measuring step or a representative value thereof and the measured value(s) of the reference miRNA(s) contained in the standard body fluid sample or a representative value thereof; and a judging step of judging the quality (degree of degradation) of the miRNA derived from the body fluid sample based on the difference(s) or the ratio(s) of the measured value(s) of the abundance(s) obtained in the comparing step.

The abundance of a reference miRNA in a body fluid sample can be investigated by measuring the reference miRNA level in an RNA sample extracted from the body fluid sample. The terms "quality of miRNA contained in a body fluid sample", "quality of miRNA in a body fluid sample", and "quality of miRNA derived from a body fluid sample" have the same meaning as the term "quality of miRNA in an RNA sample extracted from a body fluid sample".

The method can be used to evaluate the quality of miRNA contained in a body fluid sample in advance of gene expression analysis, e.g., an analysis using an array chip such as a microarray or an analysis by the polymerase chain reaction (PCR) or sequencing, to thereby judge whether the analysis can be appropriately carried out or not. Examples of the process for the gene expression analysis include: a process in which miRNA in a body fluid is labeled, and a support on which a probe(s) that captures one or more target miRNA(s) and a probe(s) that captures a reference miRNA(s) are immobilized is used to measure the expression level of each miRNA; a process in which a primer(s) that amplifies one or more target miRNA(s) and a primer(s) that amplifies a reference miRNA(s) are used to carry out amplification reaction, to thereby measure the expression level(s) of the target miRNA(s); and further, a process in which the results of these processes are utilized to carry out an analysis or a test of gene expression, for example, a test in which a clinical sample is measured so as to grasp pathological conditions.

"miRNA" is a non-coding RNA (ncRNA), which means a short-chain RNA produced in a living body having a chain length of about 15 to 25 bases, and is thought to have a function to regulate expression of mRNA. A miRNA is transcribed as an RNA (precursor) having a hairpin-like structure from genomic DNA. This precursor is cleaved by a particular enzyme, dsRNA cleavage enzyme (Drosha, Dicer) having RNase III cleavage activity, and converted into a double-stranded form and then into single strands. It is thought that the antisense strand, which is one of the double-strands, is incorporated into a protein complex called RISC, and that the RISC is involved in suppression of translation of mRNA. Thus, miRNA takes various forms in the various stages after its transcription. Therefore, when a miRNA is to be detected, various forms including the hairpin structure, double-stranded structure, and single-stranded structure need to be taken into account. The presence of miRNAs has been confirmed in various organisms.

The body fluid samples to which our method is applicable are body fluid samples separated from living bodies, and examples of the body fluid samples include, but are not limited to, body fluids such as blood, serum, plasma, urine, spinal fluid, saliva, swab, and various tissue fluids. The type of the living body from which the body fluid sample is derived is not limited, and includes various organism species. It is typically a mammal, especially human.

Possible causes of deterioration of the quality of miRNA, i.e., degradation of miRNA, in these body fluids include temperature and heat; external forces on the body fluids such as vibration and ultrasonic waves; and direct or indirect physical forces such as electric fields and magnetic fields, but the cause of quality deterioration is not limited thereto.

RNA may be extracted from these samples, and the extracted RNA may be used to measure the expression levels of miRNAs. For the extraction of RNA, a known method (for example, a method by Favaloro et al. (Favaloro et al., Methods Enzymol. 65: 718 (1980))) or a commercially available kit for RNA extraction (for example, miRNeasy, manufactured by QIAGEN; or "3D-Gene" RNA extraction reagent from liquid sample, manufactured by Toray Industries, Inc.) may be used.

Measuring Step

The abundance(s) of one or more reference miRNAs selected from miRNAs consisting of the base sequences of SEQ ID NOs:1 to 12 in a body fluid sample, and the abundance(s) of one or more reference miRNAs selected from miRNAs consisting of the base sequences of SEQ ID NOs:1 to 12 in a standard body fluid sample are measured. Concurrently with the measurement of the abundance(s) of the reference miRNA(s) in the body fluid sample, measurement of the abundance(s) of a target miRNA(s) and/or the abundance(s) of a standard nucleic acid(s) for correction may be carried out as mentioned later.

The miRNAs consisting of the base sequences of SEQ ID NOs:1 to 12 to be used as reference miRNAs are miRNAs selected as miRNAs whose abundances decrease depending on degradation of the nucleic acid sample in a body fluid sample. In general, when RNA degradation occurs, part of RNA molecules are fragmented, resulting in a decrease in the abundance of gene RNA. In this case, decrease in correlation between degraded RNA and undegraded RNA occurs among all genes detected by gene expression analysis, and thus the correlation coefficients become, for example, 0.95 or below. A reference miRNA is a miRNA whose abundance changes (decreases) in correlation with such degradation of RNA. For example, if a ratio between the expression level of a certain miRNA before RNA degradation and the expression level of the certain miRNA after RNA degradation, both of which are obtained through the later-mentioned correction process, is not more than 0.8, more preferably not more than 0.7, such a miRNA may be preferably used as a reference miRNA.

When serum (blood) is used as a body fluid sample, a miRNA whose abundance in a serum decreases more largely depending on the period of storage of the serum may be preferably selected as a reference miRNA. A miRNA whose abundance decreases depending on the storage period may be selected by, for example, preparing a serum sample from collected blood; storing the serum sample in a refrigerator (for example, at 4° C.); measuring the abundance of the miRNA in the serum sample 0 hour, 6 hours, 12 hours, 24 hours, and then subsequently every other day until 7 days after the start of the storage; and thereafter comparing the degree of decrease in the abundance. If serum samples shall be stored in a refrigerator for longer time, the storage period may be extended to, for example, 2 weeks or 1 month after the start of the storage, to measure the abundance of the miRNA and carry out the comparison. By applying a statistical method to the thus measured abundances of the miRNA obtained from the sera undergoing different storage periods and performing intergroup comparison in gene expression analysis, a miRNA whose decrease in abundance with time is statistically significant may be selected. For example, a common statistical analysis method based on the t-test or the like may be used. For example, the "SAM" package, which is based on the statistical language "R" (Tusher V G et al., Proc Natl Acad Sic USA. 2001 98 (9) 5116-5121), may be applied as it is.

In the measuring step, the abundance(s) of one or more reference miRNAs selected from particular 12 kinds of miRNAs, preferably from the 12 kinds of miRNAs consisting of the base sequences of SEQ ID NOs:1 to 12, are measured in each of a body fluid sample and a standard body fluid sample. The standard body fluid sample is a sample in which degradation of the nucleic acid sample has not proceeded, and used as a standard in judgment of the quality of miRNA contained in a body fluid sample by comparing it with the body fluid sample. The standard body fluid sample may be, for example, the same sample as the body fluid sample to be analyzed that has just been obtained or prepared, in which degradation of the nucleic acid sample contained therein has not proceeded. When the same sample as the body fluid sample to be analyzed that has just been prepared cannot be obtained, a sample prepared from the same kind of body fluid of another individual of the same organism species may be used. Or, a body fluid sample of the same organism species commercially available as a standard product may be obtained and used. When the body fluid sample is serum (blood), a sample immediately after the preparation of the serum sample (a sample undergoing 0-hour storage) may be used as a standard body fluid sample. When the serum sample immediately after the preparation cannot be obtained, a serum sample immediately after preparation (undergoing 0-hour storage) from another individual of the same organism species may be used, or a commercially available serum may be used.

The probes that capture nucleic acids such as the reference miRNAs, and the later-mentioned target miRNAs and standard nucleic acids for correction are hereinafter collectively referred to as "capture probes" or, simply, "probes".

The measurement of the abundance of miRNA may be carried out by, for example, a hybridization assay using an array chip such as a microarray in which a probe that specifically binds to the subject miRNA is immobilized on a support. An array chip comprising a support on which a "reference miRNA capture probe(s)" that captures one or more reference miRNAs is/are immobilized may be used. An array chip comprising a support on which a "target miRNA capture probe(s)" that captures the later-mentioned target miRNA(s) and a "standard nucleic acid for correction capture probe(s)" that captures a standard nucleic acid(s) for correction are further immobilized may also be used.

The "capture probe" or the "probe that captures" means a substance capable of directly or indirectly, preferably directly, and selectively binding to the miRNA to be captured. Representative examples of such a probe include nucleic acids, proteins, saccharides, and other antigenic compounds. Nucleic acid probes may be preferably used. Examples of the nucleic acids that may be used include not only DNA and RNA, but also nucleic acid derivatives such as PNA (peptide nucleic acid) and LNA (Locked Nucleic Acid). The term "derivatives" means, when used for nucleic acids, chemically modified derivatives such as labeled derivatives prepared using a fluorophore or the like; and derivatives comprising a modified nucleotide (a nucleotide containing halogen, or containing a group such as alkyl including methyl; alkoxy including methoxy; thio; or carboxymethyl; a nucleotide that has undergone, for example, reconstruction of the base, saturation of the double bonds, deamination, substitution of an oxygen molecule(s) into a sulfur molecule(s); and/or the like).

From the viewpoint of securing the stability and specificity in the hybridization, the chain length of the nucleic acid probe is preferably not less than the length of the miRNA to be detected. Usually, when the chain length is about 17 to 25 bases, the probe can sufficiently exert the selective binding capacity to the subject miRNA. Such an oligonucleic acid probe having a short chain length can be easily prepared by a well-known chemical synthesis method or the like.

The nucleic acid probe preferably has the base sequence completely complementary to the subject miRNA to be detected. However, even when there is a partial difference, the nucleic acid probe can be used as the capture probe as long as the nucleic acid probe has a base sequence which is homologous enough to allow hybridization with the subject miRNA under stringent conditions.

The stringency in the hybridization is known to be a function of the temperature, the salt concentration, the chain length of the probe, the GC content of the nucleotide sequence of the probe, and the concentration of the chaotropic agent in the hybridization buffer. As the stringent conditions, those described in Sambrook, J. et al. (1998) Molecular Cloning: A Laboratory Manual (2nd ed.), Cold Spring Harbor Laboratory Press, New York, and the like may be employed. The stringent temperature condition is not less than about 30° C. Examples of other conditions include the hybridization time, the concentration of the detergents (for example, SDS), and the presence or absence of carrier DNA. By combining these conditions, various stringencies can be set. Those skilled in the art can appropriately determine conditions to obtain the function of the capture probe provided for detection of a desired sample RNA.

Sequence information of miRNA can be obtained from a database such as GenBank or the website of miRBase. The reference miRNA capture probe(s), the target miRNA capture probe(s), and the standard nucleic acid for correction capture probe(s) can be designed based on sequence information available from these sites.

The number of the miRNA capture probe(s) immobilized on the support is not limited. For example, the abundance(s) of the miRNA(s) may be measured using a support comprising miRNA capture probes immobilized thereon, by which all known miRNAs whose sequences have been identified are comprehensively covered. Or, a support comprising a desired number of miRNA capture probes immobilized thereon, depending on the purpose of the test or the like, may be used.

As a support on which the capture probes are to be aligned and immobilized, a material like a support used in a known microarray, macroarray or the like may be used. Examples of the support include slide glasses, membranes, and beads. The support described in JP 4244788 B, which has a plurality of protruded portions on its surface, may also be used. Examples of the material of the support include, but are not limited to, inorganic materials such as glass, ceramic, and silicone; and polymers such as polyethylene terephthalate, cellulose acetate, polycarbonate, polystyrene, polymethyl methacrylate, and silicone rubber.

Examples of the known methods of immobilizing capture probes on a support include methods in which oligo-DNAs are synthesized on the surface of the support, and methods in which oligo-DNAs preliminarily synthesized are added dropwise to the surface of the support and then fixed thereon.

Examples of the former methods include the method by Ronald et al. (U.S. Pat. No. 5,705,610 B), the method by Michel et al. (U.S. Pat. No. 6,142,266 B), and the method by Francesco et al. (U.S. Pat. No. 7,037,659 B). In these methods, an organic solvent is used in the DNA synthesis reaction and, therefore, the material of the support is preferably resistant to organic solvents. In the method by Francesco et al., the DNA synthesis is controlled by irradiation with light from the back side of the support and, therefore, the material of the support is preferably a light-transmitting material.

Examples of the latter methods include the method by Hirota et al. (JP 3922454 B) and methods using a spotter. Examples of the spotting method include the pin method, which is based on mechanical contact of a pin tip with a solid phase; the ink jet method, which utilizes the principle of ink jet printers; and the capillary method, which uses a capillary. If necessary, after the spotting treatment, post-treatment such as cross-linking by UV irradiation and/or surface blocking is carried out. To allow immobilization of the oligo-DNAs through covalent bonds on the surface of the surface-treated support, functional groups such as amino groups and/or SH groups are introduced to the termini of the oligo-DNAs. The surface modification of the support is usually carried out by treatment with a silane coupling agent having an amino group and/or the like.

The hybridization with miRNA capture probes immobilized on the support is carried out by preparing, from RNA extracted from a sample, a nucleic acid sample (nucleic acid sample derived from a sample) labeled with a labeling substance, and bringing the resulting labeled nucleic acid sample into contact with the probes. Examples of the "nucleic acid sample derived from a sample" include not only RNA extracted from the sample, but also cDNA prepared by reverse transcription reaction from the RNA and cRNA. The labeled nucleic acid sample derived from a sample may be a sample prepared by directly or indirectly labeling the sample RNA with a labeling substance, or a sample prepared by directly or indirectly labeling cDNA or cRNA prepared from the sample RNA with a labeling substance.

Examples of the method of binding a labeling substance to a nucleic acid sample derived from a sample include methods in which a labeling substance is bound to the 3'-end of the nucleic acid sample, methods in which a labeling substance is bound to the 5'-end of the nucleic acid sample, and methods in which a nucleotide(s) to which a labeling substance is bound is/are incorporated into the nucleic acid. In the methods in which the labeling substance is bound to the 3'-end and the methods in which the labeling substance is bound to the 5'-end, enzymatic reaction may be used. In the enzymatic reaction, T4 RNA Ligase, Terminal Deoxitidil Transferase, Poly A polymerase, or the like may be used. Any of the labeling methods may be carried out by reference to the methods described in "Shao-Yao Ying (ed.), miRNA Experimental Protocols, Yodosha Co., Ltd. (2008)". Various kits that directly or indirectly bind a labeling substance to an RNA terminus are commercially available. Examples of kits that directly or indirectly bind a labeling substance to the 3'-end include "3D-Gene" miRNA labeling kit (Toray Industries, Inc.), miRCURY miRNA HyPower labeling kit (Exiqon), NCode miRNA Labeling system (Life Technologies), and FlashTag Biotin RNA Labeling Kit (Geni sphere).

In addition to the above, the same method as a conventional method may be used. That is, cDNA or cRNA may be synthesized from sample RNA in the presence of labeled deoxyribonucleotides or labeled ribonucleotides to prepare cDNA or cRNA in which a labeled substance is incorporated, and the resulting cDNA or cRNA may be hybridized with the probes on the array.

Examples of labeling substances that may be used include various labeling substances that are also used in known microarray analyses. Specific examples of the labeling substances include, but are not limited to, fluorescent dyes, phosphorescent dyes, enzymes, and radioisotopes. Fluorescent dyes are preferred since they can be simply measured and detected. Specific examples of the fluorescent dyes include, but are not limited to, known fluorescent dyes such as Cyanine (Cyanine 2), aminomethylcoumarin, fluorescein, indocarbocyanine (Cyanine 3), Cyanine 3.5, tetramethylrhodamine, rhodamine red, Texas red, indocarbocyanine (Cyanine 5), Cyanine 5.5, Cyanine 7, and Oyster.

As a labeling substance, luminescent semiconductor particles may also be used. Examples of such semiconductor particles include cadmium selenium (CdSe), cadmium tellurium (CdTe), indium gallium phosphide (InGaP), and silver indium zinc sulfide (AgInZnS).

The thus labeled nucleic acid sample derived from a sample is brought into contact with the miRNA capture probes on the support to allow hybridization of the nucleic acid sample with the probes. This hybridization step may be carried out in completely the same manner as the conventional hybridization step. The reaction temperature and the reaction time are appropriately selected depending on the chain length of the nucleic acid to be subjected to the hybridization. In nucleic acid hybridization, the hybridization is usually carried out at about 30° C. to 70° C. for 1 minute to ten and several hours. After hybridization and washing, the signal intensity from the labeling substance in the area where each probe is immobilized on the support is detected. Detection of the signal intensity is carried out using an appropriate signal reader depending on the type of the labeling substance. When a fluorescent dye is used as the labeling substance, a fluorescence microscope or a fluorescence scanner may be used.

The measured value of the detected fluorescence intensity is compared to the surrounding noise. More specifically, the measured value obtained from the probe-immobilized area and the measured value obtained from a position other than the probe-immobilized area are compared to each other and, when the former value is higher, the signal intensity is regarded as being detected (effectively judged positive).

When the background noise is included in the detected measured value, the background noise may be subtracted from the detected measured value. The surrounding noise may be regarded as the background noise, and subtracted from the detected measured value. In addition, the method described in "Wataru Fujibuchi and Katsuhisa Horimoto (eds.), Microarray data statistical analysis protocols, Yodosha Co., Ltd. (2008)" may be used.

Correction Process

The measured values of the abundances of the target miRNA(s) and the reference miRNA(s) obtained in the measuring step may be used as they are in the comparing step and the judging step described below. However, for example, when expression analysis of a target miRNA(s) in the body fluid sample is carried out, the measured values of the target miRNA(s) and the reference miRNA(s) may be corrected to provide the corrected measured values as the expression levels, and the resulting expression levels may be used to carry out the comparing step and the judging step. That is, the measuring step may include a process in which the measured values of the target miRNA(s) and the reference miRNA(s) are corrected.

The correction method may be a conventional method. Examples of the method include the global normalization method and the quantile normalization method. In these methods, the correction is carried out using the measured values of all miRNAs detected. The correction may also be carried out using a housekeeping RNA such as U1 snoRNA, U2 snoRNA, U3 snoRNA, U4 snoRNA, U5 snoRNA, U6 snoRNA, 5S rRNA, or 5.8S rRNA (see, for example, JP 2007-75095 A, JP 2007-97429 A), or a particular endogenous miRNA for correction (see, for example, Roberts, T. C. et al., 2014, PLoS ONE, vol. 9 (2), e89237; Chen, X. et al., 2013, PLoS ONE, vol. 8 (11), e79652; WO 2016/043170), or using an external standard nucleic acid added upon the RNA extraction or the labeling. The term "endogenous" means that the substance is not one artificially added to the sample but one naturally present in the sample. For example, "endogenous miRNA" means a miRNA naturally present in the sample and derived from the organism from which the sample was provided. When the method is applied to expression analysis of a target miRNA(s) in a body fluid sample to perform evaluation of the quality of miRNA, a correction method using an external standard nucleic acid such as a spike control, which does not depend on the sample, is preferably used.

Comparing Step

The comparing step is a step of comparing the measured value(s) of the abundance(s) of one or more reference miRNAs in the body fluid sample obtained in the measuring step or a representative value thereof to the measured value(s) of the abundance(s) of the one or more reference miRNA(s) in a standard body fluid sample or the representative value thereof, to obtain the difference(s) or the ratio(s) of the measured value(s) of the abundance(s) of the reference miRNA(s) or the representative value thereof between these samples. The difference or the ratio of the measured value(s) of the abundance(s) of the reference miRNA(s) or the representative value is typically the difference or the ratio calculated by Formulae (I) and (II). Difference of the measured values of the abundance of the reference miRNA or the representative values =(a measured value of the abundance in a body fluid sample or a representative value thereof)−(a measured value of the abundance in a standard body fluid sample or a representative value thereof)  (I)

Ratio of the measured values of the abundance of the reference miRNA or the representative values =(a measured value of the abundance in a body fluid sample or a representative value thereof)/(a measured value of the abundance in a standard body fluid sample or a representative value thereof)  (II)

The calculation may also be carried out using, instead of using Formula (I) or Formula (II), Formula (I') or Formula (II'), wherein the calculation is carried out in the reverse order. Difference of the measured values of the abundance of the reference miRNA or the representative values =(a measured value of the abundance in a standard body fluid sample or a representative value thereof)−(a measured value of the abundance in a body fluid sample or a representative value thereof)  (I')

Ratio of the measured values of the abundance of the reference miRNA or the representative values =(a measured value of the abundance in a standard body fluid sample or a representative value thereof)/(a measured value of the abundance in a body fluid sample or a representative value thereof)  (II')

The difference or the ratio of the measured value of the abundance(s) of the reference miRNA(s) or the representative value may be log-transformed after the calculation of the difference or the ratio, or each abundance in the sample may be log-transformed and thereafter the difference or the ratio may be calculated. The "logarithmic value" means a value converted to a logarithm with base 2.

As described later in the explanation of the judging step, when one miRNA among the miRNAs consisting of the base sequences of SEQ ID NOs:1 to 12 is used as a reference miRNA, the difference or the ratio between the measured value of the abundance of the reference miRNA contained in the body fluid sample and the measured value of the abundance of the reference miRNA contained in the standard body fluid sample may be calculated and used in the judgment. When a plurality of miRNAs are used as reference miRNAs, a representative value of the measured values of the abundances of the plurality of reference miRNAs contained in the body fluid sample and a representative value of the measured values of the abundances of the plurality of reference miRNAs contained in the standard body fluid sample may be calculated, and the difference or the ratio between the both representative values may be calculated and used in the judgment. As the representative value, the average or the median may be used as described later. Or, the difference or the ratio between the measured value of the abundance in the body fluid sample and the measured value of the abundance in the standard body fluid sample may be calculated for each of the reference miRNAs, and the judgment may be carried out on each of the reference miRNAs according to the prescribed criterion in the subsequent judging step, thereby judging the quality of miRNA contained in the body fluid sample.

Judging Step

The judging step is a step of judging the quality of miRNA contained in a body fluid sample based on the difference(s) or the ratio(s) between the measured value(s) of the abundance(s) of one or more reference miRNAs in the body fluid sample or a representative value thereof and the measured value(s) of the abundance(s) of the one or more reference miRNAs in the standard body fluid sample or a representative value thereof, obtained in the comparing step. In the judgment of the quality of miRNA, a threshold(s) to be used as a reference(s) to judge the quality may be set in advance for the difference(s) or the ratio(s) of the measured value(s) of the abundance(s) of the one or more reference miRNAs contained in each of the body fluid sample and the standard body fluid sample or the representative value thereof, and the quality (good or poor) may be judged based on whether the difference(s) or the ratio(s) exceed(s) the threshold(s). That is, if the difference(s) or the ratio(s) of the measured value(s) of the abundance(s) of the reference miRNA(s) or the representative value thereof obtained according to Formula (I) or Formula (II) exceed(s) the threshold(s) that has/have been optionally set in advance, the quality of miRNA contained in the body fluid sample can be judged to be good, whereas, if the difference(s) or the ratio(s) of the measured value(s) of the abundance(s) of the reference miRNA(s) or the representative value thereof is/are not more than the threshold(s), the quality of miRNA contained in the body fluid sample can be judged to be poor. Or, when the difference(s) or the ratio(s) obtained according to Formula (I') or Formula (II') is/are used, if the difference(s) or the ratio(s) is/are below the threshold(s) that has/have been arbitrarily set in advance as a reference(s), the quality of miRNA contained in the body fluid sample can be judged to be good, whereas, if the difference(s) or the ratio(s) is/are not less than the threshold(s), the quality of miRNA contained in the body fluid sample can be judged to be poor.

In the judging step, as described above, the difference(s) or the ratio(s) of the measured value(s) of the abundance(s) of the reference miRNA(s) or the representative value obtained in the comparing step may be log-transformed, and the resulting logarithmic value(s) may be used to carry out the judgment.

When one miRNA among the miRNAs consisting of the base sequences of SEQ ID NOs:1 to 12 is used as a reference miRNA, the difference or the ratio between the measured value of the abundance of the reference miRNA contained in the body fluid sample and the measured value of the abundance of the reference miRNA contained in the standard body fluid sample may be calculated in the comparing step, and the quality may be judged based on whether or not the value of the difference or the ratio exceeds the threshold to be used as a reference (when Formula (I) or (II) is used), or whether or not the value is below the threshold (when Formula (I') or (II') is used).

When a plurality of reference miRNAs among the miRNAs consisting of the base sequences of SEQ ID NOs:1 to 12 are used as the reference miRNAs, a representative value of the measured values of the abundances of the plurality of reference miRNAs contained in the body fluid sample and a representative value of the measured values of the abundances of the plurality of reference miRNAs contained in the standard body fluid sample may be calculated, and the quality may be judged based on whether or not the difference or the ratio between these representative values exceeds the threshold to be used as a reference (when Formula (I) or (II) is used), or whether or not the difference or the ratio is below the threshold (when Formula (I') or (II') is used). As the representative value, the average or the median of the abundances of the plurality of reference miRNAs may be used.

Or, when a plurality of reference miRNAs among the miRNAs consisting of the base sequences of SEQ ID NOs:1 to 12 are used as the reference miRNAs, the difference or the ratio between the measured value of the abundance in the body fluid sample and the measured value of the abundance in the standard body fluid sample may be calculated for each of the reference miRNAs, and whether or not the difference or the ratio exceeds, or is below, the threshold to be used as a reference may be judged for each of the reference miRNAs. In such cases, it is preferred to employ an additional judgement criterion by, for example, assigning the order of priority or weight to the individual judgments that are based on the plurality of reference miRNAs. When one reference miRNA is used, the one miRNA may be arbitrarily selected from the miRNAs of SEQ ID NOs:1 to 12, and a miRNA whose abundance remarkably decreases with the storage period is preferably selected. For example, one of hsa-miR-125a-3p (SEQ ID NO:1) and hsa-miR-125b-1-3p (SEQ ID NO:2) is preferably selected. When stricter or highly accurate evaluation is desired, a plurality of reference miRNAs are preferably used. For example, two to five reference miRNAs are more preferably used, and the two reference miRNAs hsa-miR-125a-3p and hsa-miR-125b-1-3p are especially preferably selected. However, as described in the following Examples, judgment of the quality can be sufficiently accurately carried out even when only one of hsa-miR-125a-3p and hsa-miR-125b-1-3p is employed as one of the plurality of reference miRNAs. When gene expression analysis is aimed at and a target miRNA to be analyzed is one of the miRNAs of SEQ ID NOs:1 to 12, a reference miRNA(s) may be selected from the miRNAs excluding the target miRNA.

The threshold to be used as a reference for the judgment may be arbitrarily set depending on, e.g., the purpose of the evaluation and the accuracy demanded. For example, the measured value(s) of the abundance(s) of a reference miRNA(s) contained in the standard body fluid sample may be used as the threshold(s).

The judging step is described hereinbelow more concretely, in which the difference(s) or the ratio(s) of the measured value(s) of the abundance(s) of a reference miRNA(s) or the representative value thereof is/are calculated according to Formula (I) or Formula (II). When the calculation is carried out according to Formula (I') or Formula (II'), an appropriate threshold may be employed in the same manner as described below, and the quality of miRNA may be judged to be good when the difference(s) or the ratio(s) is/are below the threshold.

When one reference miRNA is used, the quality can be judged by, for example, comparing the measured value of the abundance of the reference miRNA in the body fluid sample to the measured value of the abundance of the reference miRNA in the standard body fluid sample according to the judgment criterion shown by any of Formulae (1A) to (9A) and Formulae (1B) to (9B).

As shown by Formula (1A), the ratio (e/E) between the measured value e of the abundance of the reference miRNA in a body fluid sample and the measured value E of the abundance of the reference miRNA in a standard body fluid sample may be calculated, and, if the value of the obtained ratio exceeds a threshold t1, the quality of miRNA contained in the body fluid sample may be judged to be good. The threshold t1 is preferably not less than 0.7, more preferably not less than 0.8.

$$e/E > t1 \tag{1A}$$

Or, as shown by Formula (2A), the difference (e-E) between the measured value e of the abundance of the reference miRNA in a body fluid sample and the measured value E of the abundance of the reference miRNA in a standard body fluid sample may be calculated, and, if the value of the obtained difference exceeds a threshold t2, the quality of miRNA contained in the body fluid sample may be judged to be good. Since the abundance of a miRNA may vary depending on the type of the miRNA, the threshold t2 may be arbitrarily set depending on the reference miRNA used for the judgment. For example, the threshold t2 may be set within the range of −50 to 0, or, when the judgment is desired to be carried out with a stricter criterion, the threshold t2 may be set within the range of −20 to 0. For example, if the threshold t2 is set to 0 and the difference (e-E) in the measured value of the abundance is larger than 0 (a positive number), then the quality of miRNA contained in the body fluid sample may be judged to be good.

$$e - E > t2 \tag{2A}$$

Or, the measured value E of the abundance of the reference miRNA in a standard body fluid sample may be employed as a threshold t3. In this case, as shown by Formula (3A), if the measured value e of the abundance of the reference miRNA in a body fluid sample exceeds the threshold t3, that is, the measured value E of the abundance of the reference miRNA in a standard body fluid sample, then the quality of miRNA contained in the body fluid sample may be judged to be good. This corresponds to when the threshold t2 in Formula (2A) is set to 0. Accordingly, Formula (3A) corresponds to one mode of Formula (2A). That is, Formula (3A) falls within the scope of the judgment based on the difference in the measured value of the abundance.

$$e > E(=t3) \tag{3A}$$

When not only degradation of miRNA in a body fluid sample but also factors associated with the experimental procedure that may affect the measurement result should be taken into account, the judgment may be carried out using an endogenous miRNA, which is a miRNA stably present independent of degradation of RNA (hereinafter referred to as "undegradable endogenous miRNA"). The undegradable endogenous miRNA is a miRNA contained in a constant amount in a body fluid sample independent of the type thereof. Such a miRNA that shows a ratio between the measured value of its abundance before RNA degradation (at a time when degradation of the nucleic acid sample contained in a sample has not proceeded, for example, immediately after obtaining or preparing the sample) and the measured value of its abundance after RNA degradation (at a time when a certain period has passed after obtaining or preparing the sample and thus degradation of the nucleic acid sample contained therein is assumed to have proceeded) to be preferably not less than 0.90, more preferably not less than 0.95 can be selected as the undegradable endogenous miRNA. For example, hsa-miR-149-3p consisting of the base sequence of SEQ ID NO:25, or hsa-miR-4463 consisting of the base sequence of SEQ ID NO:26, can be used as an undegradable endogenous miRNA. When expression analysis of target miRNA in a body fluid sample is carried out, the "endogenous miRNA for correction" used in the correction process mentioned above can be also used as the "undegradable endogenous miRNA".

When the quality of miRNA contained in a body fluid sample is judged using an undegradable endogenous miRNA, the judgement can be carried out as follows. For example, as shown by Formula (4A), the ratio (abundance ratio e/c) between the measured value e of the abundance of the reference miRNA and the measured value c of the abundance of the undegradable endogenous miRNA in the body fluid sample, and the ratio (abundance ratio E/C) between the measured value E of the abundance of the reference miRNA and the measured value C of the abundance of the undegradable endogenous miRNA in the standard body fluid sample may be calculated and, if the ratio between these two abundance ratios exceeds a threshold t4, the quality of miRNA contained in the body fluid sample may be judged to be good.

Or, as shown by Formula (5A), the difference (abundance difference e−c) between the measured value e of the abundance of the reference miRNA and the measured value c of the abundance of the undegradable endogenous miRNA in a body fluid sample, and the difference (abundance difference E−C) between the measured value E of the abundance of the reference miRNA and the measured value C of the abundance of the undegradable endogenous miRNA in a standard body fluid sample may be calculated and, if the ratio between these two abundance differences exceeds a threshold t5, the quality of miRNA contained in the body fluid sample may be judged to be good. The thresholds t4 and t5 in these cases are preferably 0.7, more preferably 0.8.

Formula (4A) and Formula (5A) fall within the scope of the judgment based on the ratio of the measured value of the abundance.

$$(e/c)/(E/C) > t4 \tag{4A}$$

$$(e-c)/(E-C) > t5 \tag{5A}$$

Or, as shown by Formula (6A), the ratio (abundance ratio e/c) between the measured value e of the abundance of the reference miRNA and the measured value c of the abundance of the undegradable endogenous miRNA in a body fluid sample, and the ratio (abundance ratio E/C) between the measured value E of the abundance of the reference miRNA and the measured value C of the abundance of the undegradable endogenous miRNA in a standard body fluid sample may be calculated and, if the difference between these two abundance ratios exceeds a threshold t6, the quality of miRNA contained in the body fluid sample may be judged to be good.

Or, as shown by Formula (7A), the difference (abundance difference e−c) between the measured value e of the abundance of the reference miRNA and the measured value c of the abundance of the undegradable endogenous miRNA in a body fluid sample, and the difference (abundance difference E−C) between the measured value E of the abundance of the reference miRNA and the measured value C of the abundance of the undegradable endogenous miRNA in a standard body fluid sample may be calculated and, if the difference between these two abundance differences exceeds a threshold t7, the quality of miRNA contained in the body fluid sample may be judged to be good. The thresholds t6 and t7 may be set within the range of, for example, −50 to 0, and may be, for example, 0.

Formula (6A) and Formula (7A) fall within the scope of the judgment based on the difference in the measured value of the abundance.

$$(e/c) - (E/C) > t6 \tag{6A}$$

$$(e-c) - (E-C) > t7 \tag{7A}$$

Or, the ratio (abundance ratio E/C) between the measured value E of the abundance of the reference miRNA and the measured value C of the abundance of the undegradable endogenous miRNA in a standard body fluid sample may be employed as a threshold t8. In this case, as shown by Formula (8A), if the ratio (abundance ratio e/c) between the measured value e of the abundance of the reference miRNA and the measured value c of the abundance of the undegradable endogenous miRNA in a body fluid sample exceeds the threshold t8, that is, the ratio (abundance ratio E/C) between the measured value E of the abundance of the reference miRNA and the measured value C of the abundance of the undegradable endogenous miRNA in a standard body fluid sample, the quality of miRNA contained in the body fluid sample may be judged to be good. This corresponds to when Formula (6A) is employed and the threshold t6 is set to 0. Thus, Formula (8A) is one mode of Formula (6A), and falls within a scope of the judgment based on the difference in the measured value of the abundance.

Or, the difference (abundance difference E−C) between the measured value E of the abundance of the reference miRNA and the measured value C of the abundance of the undegradable endogenous miRNA in a standard body fluid sample may be employed as a threshold t9. In this case, as shown by Formula (9A), if the difference (abundance difference e–c) between the measured value e of the abundance of the reference miRNA and the measured value c of the abundance of the undegradable endogenous miRNA in a body fluid sample exceeds the threshold t9, that is, the difference (abundance difference E–C) between the measured value E of the abundance of the reference miRNA and the measured value C of the abundance of the undegradable endogenous miRNA in a standard body fluid sample, the quality of miRNA contained in the body fluid sample may be judged to be good. This corresponds to when Formula (7A) is employed and the threshold t7 is set to 0. Thus, Formula (9A) is one mode of Formula (7A), and falls within a scope of the judgment based on the difference in the measured value of the abundance.

$$e/c > E/C (=t8) \quad (8A)$$

$$e-c > E-C (=t9) \quad (9A)$$

When a plurality of miRNAs are used as reference miRNAs, a representative value of the measured values of the abundances of the plurality of reference miRNAs in a body fluid sample and a representative value of the measured values of the abundances of the plurality of reference miRNAs in a standard body fluid sample may be calculated, and the difference or the ratio between these representative values may be calculated and used in the judgment. More specifically, in the judgment criteria shown by the above-described Formula (1A) to Formula (9A), a representative value r of the measured values of the abundances of a plurality of reference miRNAs in a body fluid sample may be used instead of the measured value e of the abundance of the reference miRNA in a body fluid sample, and a representative value R of the measured values of the abundances of the plurality of reference miRNAs in a standard body fluid sample may be used instead of the measured value E of the abundance of the reference miRNA in a standard body fluid sample. That is, the judgment may be carried out using any of Formula (1B) to Formula (9B). As the representative value, the average or the median of the measured values may be used.

$$r/R > t1 \quad (1B)$$

$$r-R > t2 \quad (2B)$$

$$r > R (=t3) \quad (3B)$$

$$(r/c)/(R/C) > t4 \quad (4B)$$

$$(r-c)/(R-C) > t5 \quad (5B)$$

$$(r/c)-(R/C) > t6 \quad (6B)$$

$$(r-c)-(R-C) > t7 \quad (7B)$$

$$r/c > R/C (=t8) \quad (8B)$$

$$r-c > R-C (=t9) \quad (9B)$$

In Formula (1A) to Formula (9A), and Formula (1B) to Formula (9B) described above, taking into account the experimental error and the like, a flexibility may be given to the thresholds t1 to t9 by expanding them by an error α, thereby using the values "t1±α" to "t9±α" instead, respectively. In this case, the error α may be arbitrarily set. For example, in Formula (2A), about 10% of E may be set as a to give a flexibility to the threshold t2.

For each threshold, a log-transformed value of the measured value of the abundance may be used. In such a case, an appropriate threshold may be set depending on the transformation. For example, when Formula (1A) is applied, the abundance ratio (e/E) of the reference miRNA may be log-transformed, and the threshold t1 may be set depending on the transformation. In this case, as a result, the difference between the logarithmic values of the measured values e and E of the abundance is calculated.

Or, the difference or the ratio between the measured value of the abundance in the body fluid sample and the measured value of the abundance in the standard body fluid sample may be calculated for each of the reference miRNAs, and the judgment may be carried out individually based on every individual reference miRNA in accordance with a judgment criterion. By putting the results of individual judgments together, the quality of miRNA contained in the body fluid sample may be judged.

More specifically, for example, if the number of reference miRNAs bringing the result that the quality is good exceeds the number of reference miRNAs bringing the result that the quality is poor or exceeds an arbitrary predetermined number in the judgment by each individual reference miRNA, the overall quality of miRNA contained in the body fluid sample may be judged to be good. Conversely, if the number of reference miRNAs bringing the result that the quality is poor exceeds the number of reference miRNAs bringing the result that the quality is good or exceeds a predetermined number, the overall quality of miRNA contained in the body fluid sample may be judged to be poor. When stricter or highly accurate evaluation is desired, priority may be given to the result that the quality is judged to be poor based on one particular reference miRNA over the result that the quality is judged to be good based on a number of reference miRNAs. That is, if the one particular reference miRNA brings the result that the quality is poor, the quality of miRNA contained in the body fluid sample may be judged to be poor irrespective of the number of reference miRNAs bringing the result that the quality is good. As such one particular reference miRNA, one of hsa-miR-125a-3p (SEQ ID NO:1) and hsa-miR-125b-1-3p (SEQ ID NO:2) may be preferably employed.

We also provide a program(s) to evaluate the quality of miRNA derived from a body fluid sample in accordance with the above-described method of evaluating the quality of miRNA, the program(s) causing one or more computers to execute (i.e. containing instructions that cause one or more computers to execute):

a measured value-obtaining step of obtaining a measured value(s) of the abundance(s) of one or more reference miRNAs selected from miRNAs consisting of the base sequences of SEQ ID NOs:1 to 12 in each of a body fluid sample and a standard body fluid sample, the measured value(s) being measured by using miRNA-containing RNA samples prepared from the body fluid sample and the standard body fluid sample;

a comparing step of comparing a measured value(s) of the abundance(s) of the one or more reference miRNAs in the body fluid sample or a representative value thereof with a measured value(s) of the abundance(s) of the one or more reference miRNAs in the standard body fluid sample or a representative value thereof, to obtain a difference(s) or a ratio(s) of the measured value(s) of the abundance(s) of the one or more reference miRNAs or the representative value thereof between the body fluid sample and the standard body fluid sample; and a judging step of judging the quality of the miRNA derived from the body fluid sample based on the difference(s) or the ratio(s) of the measured value(s) of the abundance(s) of the one or more reference miRNAs or the representative value thereof obtained in the comparing step, and a computer-readable recording medium in which the program(s) is/are recorded.

For example, the program(s) may be installed in a device for analysis of the expression level of miRNA, and a measured value(s) of the expression level(s) of a reference miRNA(s) (i.e. the abundance(s) of the reference miRNA(s) in the samples) measured by an expression measurement section of the device or by an expression measurement device separate from the device may be obtained in the measured value-obtaining step, followed by carrying out each step using the measured value(s). The measured value(s) obtained may be a corrected measured value. The program(s) may include instructions that cause a computer(s) to execute a process of correcting the measured value obtained. Details of each step are as described above in relation to the method of evaluating the quality of miRNA.

The "program" is a data processing method written in an arbitrary language or by an arbitrary description method, and may be in any format including source code and binary code. The "program" is not limited to a single configuration, and includes a program having a distributed configuration as a plurality of modules and/or libraries, and a program which implements its function in cooperation with a separate program(s) represented by an OS (Operating System). A well-known constitution and procedure can be used as a specific constitution for reading the recording medium, a reading procedure, an installation procedure after the reading, and the like.

The "recording medium" may be an arbitrary "portable physical medium" (non-transient recording medium) such as a flexible disk, magnetic optical disk, ROM, EPROM, EEPROM, CD-ROM, MO, or DVD. Or, the "recording medium" may be a "communication medium" which retains the program(s) for a short period such as a communication line or a carrier wave used in transmitting the program(s) via a network represented by LAN, WAN, or internet.

We also provide a chip for miRNA quality evaluation, comprising a support on which a probe(s) that captures one or more reference miRNAs selected from miRNAs consisting of the base sequences of SEQ ID NOs:1 to 12 is/are immobilized. We also provide a chip for miRNA expression analysis, comprising a support on which a probe(s) that captures a target miRNA(s) and a probe(s) that captures one or more reference miRNAs selected from miRNAs consisting of the base sequences of SEQ ID NOs:1 to 12 are immobilized. The target miRNA(s), the one or more reference miRNAs selected from miRNAs consisting of the base sequences of SEQ ID NOs:1 to 12, the probes that capture these miRNAs, and the support on which these capture probes are immobilized are as described above.

In the chip for miRNA expression analysis, a probe(s) that captures a correcting nucleic acid(s) such as a housekeeping RNA(s), particular correcting endogenous miRNA(s), and/or external standard nucleic acid(s) added, especially a probe(s) that captures a correcting endogenous miRNA(s), to be used in the correction process may be further immobilized on the support.

One or more miRNAs selected from miR-125a-3p, miR-125b-1-3p, miR-3184-5p, miR-4443, miR-4638-5p, miR-4746-3p, miR-5572, miR-575, miR-6798-5p, miR-7110-5p, miR-88'7-3p, and miR-939-5p, preferably one or more miR-NAs selected from miRNAs consisting of the base sequences of SEQ ID NOs:1 to 12, are used as a reference miRNA(s) to measure the degree of degradation of RNA derived from a body fluid sample. When the body fluid sample is a human body fluid sample, one or more miRNAs selected from miRNAs consisting of the base sequences of SEQ ID NOs:1 to 12 may be used as a reference miRNA(s).

The term "miR-125a-3p gene" or "miR-125a-3p" includes human miR-125a-3p (that is, hsa-miR-125a-3p, miRBase Accession No. MIMAT0004602) and its homologues, orthologues and the like in other organism species. The RNA sequence shown in SEQ ID NO:1 is the sequence of hsa-miR-125a-3p. The hsa-miR-125a-3p gene can be obtained by the method described in Lagos-Quintana M et al. (2002), Curr Biol, vol. 12, pp. 735-739. The term "miR-125a-3p" includes its precursor "mir-125a", which has a hairpin-like structure. For example, the term "hsa-miR-125a-3p" includes hsa-mir-125a (miRBase Accession No. MI0000469; SEQ ID NO:13).

The term "miR-125b-1-3p gene" or "miR-125b-1-3p" includes human miR-125b-1-3p (that is, hsa-miR-125b-1-3p, miRBase Accession No. MIMAT0004592) and its homologues, orthologues and the like in other organism species. The RNA sequence shown in SEQ ID NO:2 is the sequence of hsa-miR-125b-1-3p. The hsa-miR-125b-1-3p gene can be obtained by the method described in Lagos-Quintana M et al. (2002), Curr Biol, vol. 12, pp. 735-739. The term "miR-125b-1-3p" includes its precursor "mir-125b-1", which has a hairpin-like structure. For example, the term "hsa-miR-125b-1-3p" includes hsa-mir-125b-1 (miRBase Accession No. MI0000446, SEQ ID NO:14).

The term "miR-3184-5p gene" or "miR-3184-5p" includes human miR-3184-5p (that is, hsa-miR-3184-5p, miRBase Accession No. MIMAT0015064) and its homologues, orthologues and the like in other organism species. The RNA sequence shown in SEQ ID NO:3 is the sequence of hsa-miR-3184-5p. The hsa-miR-3184-5p gene can be obtained by the method described in Stark MS et al. (2010), PLoS One, vol. 5, e9685. The term "miR-3184-5p" includes its precursor "mir-3184", which has a hairpin-like structure. For example, the term "hsa-miR-3184-5p" includes hsa-mir-3184 (miRBase Accession No. MI0014226, SEQ ID NO:15).

The term "miR-4443 gene" or "miR-4443" includes human miR-4443 (that is, hsa-miR-4443, miRBase Accession No. MIMAT0018961) and its homologues, orthologues and the like in other organism species. The RNA sequence shown in SEQ ID NO:4 is the sequence of hsa-miR-4443. The hsa-miR-4443 gene can be obtained by the method described in Jima D D et al. (2010), Blood, vol. 116, pp. 118-127. The term "miR-4443" includes its precursor "mir-4443", which has a hairpin-like structure. For example, the term "hsa-miR-4443" includes hsa-mir-4443 (miRBase Accession No. MI0016786, SEQ ID NO:16).

The term "miR-4638-5p gene" or "miR-4638-5p" includes human miR-4638-5p (that is, hsa-miR-4638-5p, miRBase Accession No. MIMAT0019695) and its homologues, orthologues and the like in other organism species. The RNA sequence shown in SEQ ID NO:5 is the sequence of hsa-miR-4638-5p. The hsa-miR-4638-5p gene can be obtained by the method described in Persson H et al. (2011), Cancer Res, vol. 71, pp. 78-86. The term "miR-4638-5p" includes its precursor "mir-4638", which has a hairpin-like structure. For example, the term "hsa-miR-4638-5p" includes hsa-miR-4638 (miRBase Accession No. MI0017265, SEQ ID NO:17).

The term "miR-4746-3p gene" or "miR-4746-3p" includes human miR-4746-3p (that is, hsa-miR-4746-3p, miRBase Accession No. MIMAT0019881) and its homologues, orthologues and the like in other organism species. The RNA sequence shown in SEQ ID NO:6 is the sequence of hsa-miR-4746-3p. The hsa-miR-4746-3p gene can be obtained by the method described in Persson H et al. (2011), Cancer Res, vol. 71, pp. 78-86. The term "miR-4746-3p" includes its precursor "mir-4746", which has a hairpin-like structure. For example, the term "hsa-miR-4746-3p" includes hsa-mir-4746 (miRBase Accession No. MI0017385, SEQ ID NO:18).

The term "miR-5572 gene" or "miR-5572" includes human miR-5572 (that is, hsa-miR-5572, miRBase Accession No. MIMAT0022260) and its homologues, orthologues and the like in other organism species. The RNA sequence shown in SEQ ID NO:7 is the sequence of hsa-miR-5572. The hsa-miR-5572 gene can be obtained by the method described in Tandon M et al. (2012), Oral Dis, vol. 18, pp. 127-131. The term "miR-5572" includes its precursor "mir-5572", which has a hairpin-like structure. For example, the term "hsa-miR-5572" includes hsa-mir-5572 (miRBase Accession No. MI0019117, SEQ ID NO:19).

The term "miR-575 gene" or "miR-575" includes human miR-575 (that is, hsa-miR-575, miRBase Accession No. MIMAT0003240) and its homologues, orthologues and the like in other organism species. The RNA sequence shown in SEQ ID NO:8 is the sequence of hsa-miR-575. The hsa-miR-575 gene can be obtained by the method described in Cummins JM et al. (2006), Proc Natl Acad Sci USA. vol. 103, pp. 3687-3692. The term "miR-575" includes its precursor "mir-575", which has a hairpin-like structure. For example, the term "hsa-miR-575" includes hsa-mir-575 (miRBase Accession No. MI0003582, SEQ ID NO:20).

The term "miR-6798-5p gene" or "miR-6798-5p" includes human miR-6798-5p (that is, hsa-miR-6798-5p, miRBase Accession No. MIMAT0027496) and its homologues, orthologues and the like in other organism species. The RNA sequence shown in SEQ ID NO:9 is the sequence of hsa-miR-6798-5p. The hsa-miR-6798-5p gene can be obtained by the method described in Ladewig E et al. (2012), Genome Research, vol. 22, pp. 1634-1645. The term "miR-6798-5p" includes its precursor "mir-6798", which has a hairpin-like structure. For example, the term "hsa-miR-6798-5p" includes hsa-mir-6798 (miRBase Accession No. MI0022643, SEQ ID NO:21).

The term "miR-7110-5p gene" or "miR-7110-5p" includes human miR-7110-5p (that is, hsa-miR-7110-5p, miRBase Accession No. MIMAT0028117) and its homologues, orthologues and the like in other organism species. The RNA sequence shown in SEQ ID NO:10 is the sequence of hsa-miR-7110-5p. The hsa-miR-7110-5p gene can be obtained by the method described in Ladewig E et al. (2012), Genome Research, vol. 22, pp. 1634-1645. The term "miR-7110-5p" includes its precursor "mir-7110", which has a hairpin-like structure. For example, the term "hsa-miR-7110-5p" includes hsa-mir-7110 (miRBase Accession No. MI0022961, SEQ ID NO:22).

The term "miR-887-3p gene" or "miR-887-3p" includes human miR-887-3 (that is, hsa-miR-887-3p, miRBase Accession No. MIMAT0004951) and its homologues, orthologues and the like in other organism species. The RNA sequence shown in SEQ ID NO:11 is the sequence of hsa-miR-887-3p. The hsa-miR-887-3p gene can be obtained by the method described in Berezikov E et al. (2006), Genome Res, vol. 16, pp. 1289-1298. The term "miR-887-3p" includes its precursor "mir-887", which has a hairpin-like structure. For example, the term "hsa-miR-887-3p" includes hsa-mir-887 (miRBase Accession No. MI0005562, SEQ ID NO:23).

The term "miR-939-5p gene" or "miR-939-5p" includes human miR-939-5p (that is, hsa-miR-939-5p, miRBase Accession No. MIMAT0004982) and its homologues, orthologues and the like in other organism species. The RNA sequence shown in SEQ ID NO:12 is the sequence of hsa-miR-939-5p. The hsa-miR-939-5p gene can be obtained by the method described in Lui WO et al. (2007), Cancer Res, vol. 67, pp. 6031-6043. The term "miR-939-5p" includes its precursor "mir-939", which has a hairpin-like structure. For example, the term "hsa-miR-939-5p" includes hsa-mir-939 (miRBase Accession No. MI0005761, SEQ ID NO:24).

EXAMPLES

Our methods, including the process of selecting the reference miRNA(s) dependent on degradation of RNA, are described below more concretely by way of Examples. However, this disclosure is not limited to the following Examples.

Example 1

Selection of Reference miRNA(s)

DNA Microarray

Using a "3D-Gene" human miRNA oligo chip (based on miRBase release 21), manufactured by Toray Industries, Inc., the following experiment was carried out.

Preparation of Serum Samples

From each of three healthy human individuals, blood was collected, and serum was prepared therefrom. The serum obtained was aliquoted in 300-µL volumes to provide six samples per individual, and five out of the six samples were left to stand in a refrigerator whose temperature was set to 4° C. One sample from each individual was immediately stored in a freezer whose temperature was set to −80° C. (Hour 0). The serum samples left to stand in the refrigerator were taken out at Hour 6, Hour 24, Hour 48, Hour 72, and Hour 168, respectively, and then stored in a freezer whose temperature was set to −80° C. The samples stored in the freezer at −80° C. were left to stand as they are until the RNA extraction operation described below.

Preparation of Sample RNAs and Measurement of miRNA Expression Levels

The sera prepared and left to stand in the freezer as described above were thawed at the same time, and RNAs contained in the serum samples (hereinafter referred to as sample RNAs) were extracted. For the extraction, a "3D-Gene" RNA extraction reagent from liquid sample kit (Toray Industries, Inc.) was used.

The obtained sample RNAs were labeled using a "3D-Gene" miRNA labeling kit (Toray Industries, Inc.). In the labeling, an external standard nucleic acid was added to correct the measured value of miRNA to the expression level. The labeled sample RNAs were subjected to hybridization using a "3D-Gene" miRNA chip (Toray Industries, Inc.) according to the manufacturer's standard protocol. The DNA microarray after the hybridization was subjected to a microarray scanner (Toray Industries, Inc.) to measure the fluorescence intensities. Settings of the scanner were as follows: laser output, 100%; photomultiplier voltage, AUTO.

The measured value for each miRNA detected with the DNA microarray was converted to a logarithm with base 2, and then subjected to correction with the external standard nucleic acid added upon the labeling, to obtain the expression level of each miRNA.

As described above, the sera left to stand at 4° C. for 0, 6, 24, 48, 72, or 168 hours were subjected three times to measurement of the expression level of each miRNA at the time when each standing time has passed, and then the average of the measurement results was obtained.

Selection of Reference miRNAs

The expression levels of the miRNAs in each serum sample obtained as described above were compared, and miRNAs showing a larger change in the expression level (the abundance in the sample) depending on the standing time were extracted to select reference miRNAs.

First, using the expression level of each miRNA in the Hour 0 sample as a reference, the ratio of the expression level of each miRNA in each of the Hour 6, Hour 24, Hour 48, Hour 72, and Hour 168 samples to the reference ((the expression level at Hour 6, 24, 48, 72, or 168)/the expression level at Hour 0) was obtained.

Subsequently, the miRNAs detected were narrowed down to miRNAs stably detected in the high-expression range.

To select miRNAs whose expression levels were more largely changed depending on the length of the standing time from the narrowed-down miRNAs, the "SAM" package, which is based on the statistical language "R" (Tusher VG et al., Proc Natl Acad Sic USA. 2001 98 (9) 5116-5121), was used to extract miRNAs whose SAM statistic was −1 or less. The top 12 miRNAs extracted and their expression level ratios are shown in Table 1.

Each of the miRNAs (SEQ ID NOs:1 to 12) in Table 1 showed a successive decrease in the expression level when stored at 4° C., which is a condition in which miRNA in serum is relatively unstable, and the degree of the decrease in the expression level was large. Since the correlation coefficient between the expression levels of total miRNA detected in the serum sample stored in the refrigerator for 0 hour and the serum sample stored in the refrigerator for 168 hours was 0.95 or less, we confirmed that degradation of RNA in the serum sample had proceeded at the time when 168 hours had passed. Thus, we confirmed that the miRNAs shown in Table 1 can be used as miRNA indices whose expression levels (the abundances in the sample) change with time depending on degradation of RNA contained in a serum sample. That is, we found that the quality (degree of degradation) of miRNA in a serum sample can be known by measuring the expression level(s) of a miRNA(s) shown in Table 1. In particular, hsa-miR-125a-3p (SEQ ID NO:1) and hsa-miR-125b-1-3p (SEQ ID NO:2) showed sharp changes from an early stage (Hour 48), and therefore they were found to be suitable for more accurate evaluation of the quality.

TABLE 1

Changes in the expression levels of miRNAs with time in the serum sample stored at 4° C.

| Name of miRNA | SAM statistic | Standing time | | | | |
|---|---|---|---|---|---|---|
| | | 6 hours | 24 hours | 48 hours | 72 hours | 168 hours |
| hsa-miR-125a-3p (SEQ ID NO: 1) | −2.4 | 0.99 | 0.93 | 0.81 | 0.75 | 0.33 |
| hsa-miR-125b-1-3p (SEQ ID NO: 2) | −1.5 | 1.00 | 0.91 | 0.79 | 0.71 | 0.43 |
| hsa-miR-3184-5p (SEQ ID NO: 3) | −1.4 | 1.09 | 1.04 | 0.97 | 0.87 | 0.60 |
| hsa-miR-4443 (SEQ ID NO: 4) | −1.1 | 1.03 | 1.00 | 0.94 | 0.90 | 0.67 |
| hsa-miR-4638-5p (SEQ ID NO: 5) | −1.1 | 1.02 | 1.04 | 0.96 | 0.92 | 0.49 |
| hsa-miR-4746-3p (SEQ ID NO: 6) | −1.1 | 1.03 | 1.02 | 0.95 | 0.89 | 0.68 |
| hsa-miR-5572 (SEQ ID NO: 7) | −1.2 | 1.04 | 1.04 | 0.91 | 0.88 | 0.58 |
| hsa-miR-575 (SEQ ID NO: 8) | −1.1 | 1.13 | 1.13 | 1.05 | 0.97 | 0.63 |
| hsa-miR-6798-5p (SEQ ID NO: 9) | −1.0 | 1.05 | 1.06 | 1.01 | 0.96 | 0.78 |
| hsa-miR-7110-5p (SEQ ID NO: 10) | −1.3 | 1.06 | 1.05 | 0.97 | 0.86 | 0.60 |
| hsa-miR-887-3p (SEQ ID NO: 11) | −1.1 | 1.10 | 1.10 | 1.03 | 0.97 | 0.65 |
| hsa-miR-939-5p (SEQ ID NO: 12) | −1.2 | 1.05 | 1.05 | 0.95 | 0.92 | 0.63 |

Based on the results of Example 1, the threshold of the expression level ratio of each reference miRNA in the following Examples 2 to 6 was set to 0.8, and the quality of miRNA contained in each sample was judged to be good when the ratio exceeded this threshold.

Example 2

From one healthy human individual, blood was collected, and a serum sample was prepared therefrom. The obtained serum was aliquoted in 300-μL volumes and immediately stored in a freezer whose temperature was set to −80° C. For RNA extraction, a "3D-Gene" RNA extraction reagent from liquid sample kit (Toray Industries, Inc.) was used.

The obtained sample RNA was labeled with a "3D-Gene" miRNA labeling kit (Toray Industries, Inc.), and an external standard nucleic acid was added to correct the measured value of miRNA into the expression level. The labeled sample-derived RNAs were subjected to hybridization using a "3D-Gene" miRNA chip (Toray Industries, Inc.) according to the manufacturer's standard protocol. The DNA microarray after the hybridization was subjected to a microarray scanner (Toray Industries, Inc.) to measure the fluorescence intensities. Settings of the scanner were as follows: laser output, 100%; photomultiplier voltage, AUTO. The signal values of miRNAs detected were corrected with the signal value of the external standard nucleic acid, to obtain the expression levels.

As a reference miRNA to be used for judgment of the quality, hsa-miR-125b-1-3p (SEQ ID NO:2) was selected. A commercially available serum sample was used as a standard body fluid sample in which degradation of the nucleic acid sample had not proceeded. In the same manner as described above, the expression level of hsa-miR-125b-1-3p contained in the standard body fluid sample was obtained.

The expression level of hsa-miR-125b-1-3p derived from the serum sample was divided by the expression level of hsa-miR-125b-1-3p derived from the standard body fluid sample, to calculate the expression level ratio between them. As a result, the expression level ratio was 0.99. Since it was higher than the threshold 0.8, the quality of miRNA contained in this serum sample was judged to be good.

On the other hand, since the correlation coefficient between the detected expression level of total miRNA derived from the serum sample and the expression level of total miRNA derived from the standard body fluid sample was 0.99, the miRNA was shown to be of good quality and free of degradation. This was consistent with the above-described result of judgment of good quality.

Example 3

As reference miRNAs for judgment of the quality, two kinds of miRNAs, hsa-miR-125b-1-3p (SEQ ID NO:2) and hsa-miR-6798-5p (SEQ ID NO:9), were used instead of hsa-miR-125b-1-3p (SEQ ID NO:2). Except for this, the same experiment as in Example 2 was carried out to measure the expression levels of these two kinds of miRNAs derived from each of the serum sample and the standard body fluid sample.

The expression levels in these samples were compared using the average of the expression levels of the two kinds of miRNAs as a representative value. By dividing the representative value for the serum sample by the representative value for the standard body fluid sample, the expression level ratio was calculated. As a result, the expression level ratio was 0.98. Since it was higher than the threshold 0.8, the quality of miRNA contained in this serum sample was judged to be good.

On the other hand, since the correlation coefficient between the detected expression level of total miRNA derived from the serum sample and the expression level of total miRNA derived from the standard body fluid sample was 0.99, the miRNA was shown to be of good quality and free of degradation. This was consistent with the above-described result of judgment of good quality.

Example 4

In the same manner as in Example 3 except that the serum sample was changed to a serum sample that had been left to stand at 4° C. for 168 hours following its preparation, the expression levels of the two kinds of miRNAs (hsa-miR-125b-1-3p (SEQ ID NO:2) and hsa-miR-6798-5p (SEQ ID NO:9)) derived from each of the serum sample and the standard body fluid sample were measured. The average of the expression levels of the two kinds of miRNAs was used as a representative value, and the expression level ratio was calculated from the representative value.

As a result, the expression level ratio was 0.34. Since it was lower than the threshold 0.8, the quality of miRNA contained in this serum sample was judged to be poor.

On the other hand, since the correlation coefficient between the detected expression level of total miRNA derived from the serum sample and the expression level of total miRNA derived from the standard body fluid sample was as low as 0.93, the miRNA was shown to have been degraded, causing deterioration of the quality. This was consistent with the above-described result of judgment of good quality.

Example 5

In the same manner as in Example 3 except that the serum sample was changed to a serum sample that had been left to stand at 4° C. for 72 hours following its preparation, the expression levels of the two kinds of miRNAs (hsa-miR-125b-1-3p (SEQ ID NO:2) and hsa-miR-6798-5p (SEQ ID NO:9)) derived from each of the serum sample and the standard body fluid sample were measured. The expression level ratio of hsa-miR-125b-1-3p and the expression level ratio of hsa-miR-6798-5p were calculated, and comparison of the expression levels was carried out.

As a result, the expression level ratio of hsa-miR-6798-5p was 0.95, which was higher than the threshold 0.8. However, the expression level ratio of hsa-miR-125b-1-3p was 0.73, which was lower than the threshold 0.8. Since one of the two kinds of reference miRNAs showed a value lower than the threshold, the quality of miRNA contained in the sample was judged to be poor.

On the other hand, the correlation coefficient between the detected expression level of total miRNA and the expression level of total miRNA derived from the standard body fluid sample was 0.94, which was a slightly low value. Thus, the miRNA was shown to have been degraded, causing slight deterioration of the quality. This was consistent with the above-described result of judgment of good quality.

Comparative Example 1

To compare our method of evaluating the quality of miRNA to a method by electrophoresis, which is a conventional quality evaluation method, evaluation of the quality by electrophoresis was carried out using the serum samples used in the above-described Examples 4 and 5.

As a result, according to the results of electrophoresis, the difference in the quality (degree of degradation) between RNA extracted from the serum sample that had been left to stand for 72 hours or 168 hours and RNA extracted from a commercially available serum sample, which was a standard body fluid sample in which degradation of the nucleic acid sample had not proceeded, could not be identified.

Comparative Example 2

As a reference miRNA for judgment of the quality, hsa-miR-149-3p (SEQ ID NO:25) was used instead of hsa-miR-125b-1-3p (SEQ ID NO:2), and a serum sample that had been left to stand at 4° C. for 168 hours following its preparation was used. Except for these, the same experiment as in Example 2 was carried out to measure the expression level of the reference miRNA derived from each of the serum sample and the standard body fluid sample. hsa-miR-149-3p used as a reference miRNA is one of the miRNAs whose expression levels were most stable and did not change (decrease) with the standing time in the above-described Example 1.

As a result, the expression level ratio was 0.98, which was higher than the threshold 0.8. When the evaluation was carried out with the same criterion as in our method, the quality of miRNA contained in the sample was judged to be good. However, since the correlation coefficient between the detected expression level of total miRNA derived from the serum sample and the expression level of total miRNA derived from the standard body fluid sample was 0.94, it was shown that degradation of miRNA had actually occurred, causing deterioration of the quality. That is, judgment of the quality could not be carried out correctly when hsa-miR-149-3p, which is not included in the reference miRNAs that can be used in our method, was used.

Example 6

As in Example 2, hsa-miR-125b-1-3p (SEQ ID NO:2) was used as a reference miRNA for judgment of the quality.

In addition, hsa-miR-4463 (SEQ ID NO:26), which is an undegradable endogenous miRNA independent of RNA degradation, was also used. The expression levels of these two kinds of miRNAs derived from each of the serum sample and the standard body fluid sample were measured. For each of the serum sample and the standard body fluid sample, the expression level of hsa-miR-125b-1-3p was divided by the expression level of hsa-miR-4463 to calculate the expression level ratio, and then the expression level ratio derived from the serum sample was divided by the expression level ratio derived from the standard body fluid sample to calculate the ratio between the expression level ratios, which was then compared to the threshold.

As a result, the expression level ratio obtained by dividing the expression level of hsa-miR-125b-1-3p by the expression level of hsa-miR-4463 was 0.97 in the serum sample, and 0.98 in the standard body fluid sample. The ratio between these expression level ratios was 0.99. Since it was higher than the threshold 0.8, the quality of miRNA contained in the sample was judged to be good.

On the other hand, since the correlation coefficient between the expression level of total miRNA derived from the serum sample and the expression level of total miRNA derived from the standard body fluid sample was 0.99, the miRNA was shown to be of good quality and free of degradation. This was consistent with the above-described result of judgment of good quality.

The invention claimed is:

1. A method of evaluating quality of miRNA derived from a body fluid sample, the method being carried out by a device for analysis of the expression level of miRNA and comprising:

obtaining, with a device, a measured value(s) or a corrected measured value(s) of the abundance(s) of one or more reference miRNAs selected from miRNAs consisting of base sequences of SEQ ID NOs:1 to 12 in each of miRNA-containing RNA samples prepared from a body fluid sample and a standard body fluid sample;

comparing, with the device, the obtained value(s) of the abundance(s) of the one or more reference miRNAs in the body fluid sample or a representative value thereof to the obtained value(s) of the abundance(s) of the one or more reference miRNAs in the standard body fluid sample or a representative value thereof, to obtain a difference(s) or a ratio(s) of the obtained value(s) of the abundance(s) of the one or more reference miRNAs or the representative value thereof between the body fluid sample and the standard body fluid sample; and judging, with the device, the quality of the miRNA derived from the body fluid sample by comparing the difference(s) or the ratio(s) of the obtained value(s) of the abundance(s) of the one or more reference miRNAs or the representative value thereof with a threshold(s) predetermined as a criterion(criteria), wherein said difference(s) is/are calculated by subtracting the obtained value(s) of the abundance(s) in the standard body fluid sample or the representative value thereof from the obtained value(s) of the abundance(s) in the body fluid sample or the representative value thereof, or said ratio(s) is/are calculated by dividing the obtained value(s) of the abundance(s) in the body fluid sample or the representative value thereof by the obtained value(s) of the abundance(s) in the standard body fluid sample or the representative value thereof, wherein the body fluid sample is judged to have a good quality when the difference(s) or the ratio(s) exceed(s) the threshold(s); and obtaining a result of miRNA expression analysis on the body fluid sample judged to have a good quality.

2. The method according to claim 1, wherein the judging step is a step of obtaining a difference or a ratio of the measured value of the abundance of one reference miRNA, differences or ratios of the measured values of the abundances of a plurality of reference miRNAs, respectively, or a difference or a ratio of the representative value of the measured values of the abundances of a plurality of reference miRNAs.

3. The method according to claim 1, wherein the representative value of the obtained values of the abundances of the one or more reference miRNAs in each of the body fluid sample and the standard body fluid sample is an average or a median of the obtained values of the abundances of the one or more reference miRNAs.

4. The method according to claim 1, wherein the method comprises obtaining, with the device, a measured value(s) of said one or more reference miRNAs in each of said miRNA-containing RNA samples, and correcting, with the device, the obtained measured values(s), and wherein the subsequent steps are carried out using the corrected measured value(s).

5. The method according to claim 1, wherein the measured value(s) is/are a value(s) measured by carrying out hybridization by bringing a probe(s) that captures the one or more reference miRNAs, the probe(s) being immobilized on a support, into contact with each of nucleic acid samples extracted from the body fluid sample and the standard body fluid sample and labeled with a labeling substance, respectively.

6. The method according to claim 5, wherein the support further comprises a probe(s) that captures the target miRNA(s) immobilized thereon.

7. The method according to claim 1, wherein the body fluid sample is blood, serum, or plasma.

* * * * *

SEQUENCE LISTING

```
<160> NUMBER OF SEQ ID NOS: 26

<210> SEQ ID NO 1
<211> LENGTH: 22
<212> TYPE: RNA
<213> ORGANISM: Homo sapiens

<400> SEQUENCE: 1
acaggugagg uucuugggag cc                                              22

<210> SEQ ID NO 2
<211> LENGTH: 22
<212> TYPE: RNA
<213> ORGANISM: Homo sapiens

<400> SEQUENCE: 2
acggguuagg cucuugggag cu                                              22

<210> SEQ ID NO 3
<211> LENGTH: 24
<212> TYPE: RNA
<213> ORGANISM: Homo sapiens

<400> SEQUENCE: 3
ugaggggccu cagaccgagc uuuu                                            24

<210> SEQ ID NO 4
<211> LENGTH: 17
<212> TYPE: RNA
<213> ORGANISM: Homo sapiens

<400> SEQUENCE: 4
uuggaggcgu ggguuuu                                                    17

<210> SEQ ID NO 5
```

-continued

```
<211> LENGTH: 21
<212> TYPE: RNA
<213> ORGANISM: Homo sapiens

<400> SEQUENCE: 5
acucggcugc gguggacaag u                                              21

<210> SEQ ID NO 6
<211> LENGTH: 21
<212> TYPE: RNA
<213> ORGANISM: Homo sapiens

<400> SEQUENCE: 6
agcggugcuc cugcgggccg a                                              21

<210> SEQ ID NO 7
<211> LENGTH: 21
<212> TYPE: RNA
<213> ORGANISM: Homo sapiens

<400> SEQUENCE: 7
guuggggugc aggggucugc u                                              21

<210> SEQ ID NO 8
<211> LENGTH: 19
<212> TYPE: RNA
<213> ORGANISM: Homo sapiens

<400> SEQUENCE: 8
gagccaguug gacaggagc                                                 19

<210> SEQ ID NO 9
<211> LENGTH: 23
<212> TYPE: RNA
<213> ORGANISM: Homo sapiens

<400> SEQUENCE: 9 ccaggggggau gggcgagcuu ggg                                           23

<210> SEQ ID NO 10
<211> LENGTH: 21
<212> TYPE: RNA
<213> ORGANISM: Homo sapiens

<400> SEQUENCE: 10 uggggggugug gggagagaga g                                             21

<210> SEQ ID NO 11
<211> LENGTH: 22
<212> TYPE: RNA
<213> ORGANISM: Homo sapiens

<400> SEQUENCE: 11
gugaacgggc gccaucccga gg                                             22

<210> SEQ ID NO 12
<211> LENGTH: 24
<212> TYPE: RNA
<213> ORGANISM: Homo sapiens

<400> SEQUENCE: 12
uggggagcug aggcucuggg ggug                                           24
```

```
<210> SEQ ID NO 13
<211> LENGTH: 86
<212> TYPE: RNA
<213> ORGANISM: Homo Sapiens

<400> SEQUENCE: 13
ugccagucuc uaggucccug agacccuuua accugugagg acauccaggg ucacagguga    60
gguucuuggg agccuggcgu cuggcc                                        86

<210> SEQ ID NO 14
<211> LENGTH: 75
<212> TYPE: RNA
<213> ORGANISM: Homo Sapiens

<400> SEQUENCE: 14
aagcaagacu gaggggccuc agaccgagcu uuuggaaaau agaaaagucu cgcucucugc    60
cccucagccu aacuu                                                    75

<210> SEQ ID NO 15
<211> LENGTH: 75
<212> TYPE: RNA
<213> ORGANISM: Homo Sapiens

<400> SEQUENCE: 15
aagcaagacu gaggggccuc agaccgagcu uuuggaaaau agaaaagucu cgcucucugc    60
cccucagccu aacuu                                                    75

<210> SEQ ID NO 16
<211> LENGTH: 68
<212> TYPE: RNA
<213> ORGANISM: Homo Sapiens

<400> SEQUENCE: 16
gacucggcug cgguggacaa guccggcucc agaaccugga caccgcucag ccggccgcgg    60
caggggguc                                                           68

<210> SEQ ID NO 17
<211> LENGTH: 68
<212> TYPE: RNA
<213> ORGANISM: Homo Sapiens

<400> SEQUENCE: 17
gacucggcug cgguggacaa guccggcucc agaaccugga caccgcucag ccggccgcgg    60
caggggguc                                                           68

<210> SEQ ID NO 18
<211> LENGTH: 71
<212> TYPE: RNA
<213> ORGANISM: Homo Sapiens

<400> SEQUENCE: 18
gugucugugc cgguccagg agaaccugca gaggcaucgg gucagcggug cuccugcggg    60
ccgacacuca c                                                        71

<210> SEQ ID NO 19
<211> LENGTH: 137
<212> TYPE: RNA
<213> ORGANISM: Homo Sapiens

<400> SEQUENCE: 19
```

| | |
|---|---|
| agccagacaa gagggucaug gggagucacu gucaacccag agcaggcacu gccccugcga | 60 |
| ccagccuggg gcaucgguug gggugcaggg gucugcuggu gaugcuuucc aucucuuugc | 120 |
| uuuguccuga uuguagc | 137 |

```
<210> SEQ ID NO 20
<211> LENGTH: 94
<212> TYPE: RNA
<213> ORGANISM: Homo Sapiens

<400> SEQUENCE: 20
```

| | |
|---|---|
| aauucagccc ugccacuggc uuaugucaug accuugggcu acucaggcug ucugcacaau | 60 |
| gagccaguug gacaggagca gugccacuca acuc | 94 |

```
<210> SEQ ID NO 21
<211> LENGTH: 67
<212> TYPE: RNA
<213> ORGANISM: Homo Sapiens

<400> SEQUENCE: 21
```

| | |
|---|---|
| ggcagccagg gggaugggcg agcuuggggcc cauuccuuuc cuuacccuac ccccauccc | 60 |
| ccuguag | 67 |

```
<210> SEQ ID NO 22
<211> LENGTH: 86
<212> TYPE: RNA
<213> ORGANISM: Homo Sapiens

<400> SEQUENCE: 22
```

| | |
|---|---|
| ggggcugggg guguggggag agagagugca cagccagcuc agggauuaaa gcucuuucuc | 60 |
| ucucucucuc ucccacuucc cugcag | 86 |

```
<210> SEQ ID NO 23
<211> LENGTH: 79
<212> TYPE: RNA
<213> ORGANISM: Homo Sapiens

<400> SEQUENCE: 23
```

| | |
|---|---|
| gugcagaucc uugggagccc uguuagacuc uggauuuuac acuuggagug aacgggcgcc | 60 |
| aucccgaggc uuugcacag | 79 |

```
<210> SEQ ID NO 24
<211> LENGTH: 82
<212> TYPE: RNA
<213> ORGANISM: Homo Sapiens

<400> SEQUENCE: 24
```

| | |
|---|---|
| ugugggcagg gcccuggggga gcugaggcuc uggggguggc cggggcugac ccugggccuc | 60 |
| ugcuccccag ugucugaccg cg | 82 |

```
<210> SEQ ID NO 25
<211> LENGTH: 21
<212> TYPE: RNA
<213> ORGANISM: Homo sapiens

<400> SEQUENCE: 25
```

| | |
|---|---|
| agggagggac gggggcugug c | 21 |

```
<210> SEQ ID NO 26
<211> LENGTH: 17
```

```
<212> TYPE: RNA
<213> ORGANISM: Homo sapiens

<400> SEQUENCE: 26
gagacugggg uggggcc                                                17
```